United States Patent
Kim et al.

(10) Patent No.: US 11,660,342 B2
(45) Date of Patent: May 30, 2023

(54) METHOD FOR INCREASING PERMEABILITY OF BLOOD-BRAIN BARRIER

(71) Applicant: POSTECH Research and Business Development Foundation, Pohang-si (KR)

(72) Inventors: Won Jong Kim, Pohang-si (KR); Taejeong Kim, Pohang-si (KR)

(73) Assignee: POSTECH RESEARCH AND BUSINESS DEVELOPMENT FOUNDATION, Pohang-si (KR)

( * ) Notice: Subject to any disclaimer, the term of this patent is extended or adjusted under 35 U.S.C. 154(b) by 129 days.

(21) Appl. No.: 17/198,419

(22) Filed: Mar. 11, 2021

(65) Prior Publication Data

US 2021/0290762 A1    Sep. 23, 2021

(30) Foreign Application Priority Data

Mar. 19, 2020  (KR) ........................ 10-2020-0033940

(51) Int. Cl.
| | |
|---|---|
| *A61K 41/00* | (2020.01) |
| *A61K 33/24* | (2019.01) |
| *A61K 38/06* | (2006.01) |
| *A61P 25/16* | (2006.01) |
| *A61P 25/28* | (2006.01) |
| *A61K 9/51* | (2006.01) |

(52) U.S. Cl.
CPC ........ *A61K 41/0028* (2013.01); *A61K 9/5138* (2013.01); *A61K 33/24* (2013.01); *A61K 38/063* (2013.01); *A61P 25/16* (2018.01); *A61P 25/28* (2018.01)

(58) Field of Classification Search
CPC .. A61K 41/0028; A61K 33/24; A61K 38/063; A61K 9/5138; A61P 25/28; A61P 25/16
USPC ...................................................... 514/740
See application file for complete search history.

(56) References Cited

U.S. PATENT DOCUMENTS

| 2005/0074506 A1 | 4/2005 | Natan et al. |
| 2014/0050718 A1 | 2/2014 | Thorne et al. |

FOREIGN PATENT DOCUMENTS

| JP | 2003-523965 | 8/2003 |
| JP | 2019-191518 | 10/2019 |
| KR | 20190011615 | 2/2019 |
| KR | 10 2020 0015251 | 2/2020 |

OTHER PUBLICATIONS

Renée J. Turner et al., "IImplications of MMP9 for Blood Brain Barrier Disruption and Hemorrhagic Transformation Following Ischemic Stroke", Front. Cell. Neurosci., Mar. 4, 2016.
Ralf G. Rempe et al., "Matrix Metalloproteinase-Mediated Blood-Brain Barrier Dysfunction in Epilepsy", The Journal of Neuroscience, May 2, 2018 • 38(18):4301-4315.
Susana R. Parathath et al., "Nitric oxide mediates neurodegeneration and breakdown of the blood-brain barrier in tPA-dependent excitotoxic injury in mice", Journal of Cell Science 2006 119: 339-349; doi: 10.1242/jcs.02734.
Lisa A. Ridnour et al., "Nitric oxide regulates matrix metalloproteinase-9 activity by guanylyl-cyclase-dependent and-independent pathways", PNAS Oct. 23, 2007 104 (43) 16898-16903; https://doi.org/10.1073/pnas.0702761104.
Zezong Gu et al., "S-Nitrosylation of Matrix Metalloproteinases: Signaling Pathway to Neuronal Ceil Death", SCIENCE, vol. 297, Aug. 16, 2002.
KIPO, Decision to Grant of Application No. 10-2020-0033940, dated Jan. 12, 2023.
EPO, Search Report of EP 21161851.7 dated Sep. 16, 2021.
Cijun Shuai et al., "Functionalized BaTiO3 enhances piezoelectric effect towards cell response of bone scaffold", Colloids and Surfaces B: Biointerfaces, vol. 185, Jan. 1, 2020, 110587.
Youngnam Kang et al., "Tumor vasodilation by N-Heterocyclic carbene-based nitric oxide delivery triggered by high-intensity focused ultrasound and enhanced drug homing to tumor sites for anti-cancer therapy", Biomaterials, Oct. 2019;217:119297. doi: 10.1016/j.biomaterials.2019.119297. Epub Jun. 21, 2019.
Aanchal Aggarwal et al., "S-nitrosoglutathione prevents blood-brain barrier disruption associated with increased matrix metalloproteinase-9 activity in experimental diabetes", J Neurochem, Mar. 2015;132(5):595-608. doi: 10.1111/jnc.12939. Epub Oct. 17, 2014.
Victoria E. Thiel et al., "Forum Mini-Review Nitric Oxide and Blood-Brain Barrier Integrity", Antioxidants & Redox Signaling, 2001, vol. 3, No. 2, pp. 273-278.
Cijun Shuai et al., "Functionalized BaTiO3 enhances piezoelectric effect towards cell response of bone scaffold", Colloids and Surfaces B Biointerfaces, 2019, vol. 185, No. 110587.
JPO, Office Action of JP 2021-045149 dated Apr. 26, 2022.

*Primary Examiner* — Kristin A Vajda
(74) *Attorney, Agent, or Firm* — Lex IP Meister, PLLC

(57) ABSTRACT

The present invention relates to a method for increasing the blood-brain barrier permeability, and more particularly, to a method for increasing the blood-brain barrier permeability, the method including: (S1) a step of delivering a nanogenerator carrying a nitric oxide (NO) donor to a site adjacent to the blood-brain barrier; (S2) a step of delivering a first triggering stimulus to an area where the nanogenerator has been delivered so as to release nitric oxide from the nanogenerator; and (S3) a step of allowing the released nitric oxide to activate matrix metallopeptidase-9 (MMP-9) and inducing the activated MMP-9 to weaken the tight junction between a cerebrovascular endothelial cell and another cerebrovascular endothelial cell.

9 Claims, 22 Drawing Sheets

$C_{14}H_{22}N_4O_2$
Calculated Mass:278.17

(1) NG administration (2) US-guided HIFU irradiation

*Fear conditioning*     *Fear recall*

● (I) Healthy  △ (II) Saline  ▣ (III) NG w/ HIFU
⬠ (IV) HIFU interval  ○ (V) NG w/ HIFU interval

METHOD FOR INCREASING PERMEABILITY OF BLOOD-BRAIN BARRIER

CROSS-REFERENCE TO RELATED APPLICATION

This application claims priority to Korean Patent Application No. 10-2020-0033940 filed on Mar. 19, 2020, the disclosure of which is incorporated by reference herein in its entirety.

BACKGROUND OF THE INVENTION

Field of the Invention

The present invention relates to a method for increasing the blood-brain barrier (BBB) permeability, and more particularly, to a method for increasing the blood-brain barrier permeability by opening the blood-brain barrier using a nitric oxide donor-carrying nanogenerator and a triggering stimulus to be applied thereto, and allowing a desired substance to be accumulated in the deep part of the brain.

Description of the Related Art

The blood-brain barrier is a defense system existing in a living body and plays the role of preventing foreign materials such as bacteria and viruses, which have flowed in along the blood vessels, from penetrating into the deep part of the brain. Such a defense system is crucial for protecting the brain; however, there is also a problem that the defense system prevents an artificially administered functional drug from flowing into the brain. There are a method of directly administering a drug into the brain through a surgery and a method of injecting a drug into the cerebrospinal fluid; however, those methods have limitations in terms of high risk, high cost, and low level of convenience for the patient.

Many drugs have been developed for the treatment of various brain diseases; however, treatments using existing drug systems have significant limitations due to the blood-brain barrier. Therefore, there is a demand for a new composition or drug delivery system, which can deliver a drug in a non-invasive manner but does not interfere with the form or efficacy of the drug.

On the other hand, neurodegenerative diseases cause cognitive impairment and/or physical disability such as memory loss, dementia, and tremors, and these diseases are widely spreading among millions of people over the world. Deep brain stimulation (DBS) is one of clinical therapeutic methods effective for alleviating various neurological symptoms in Parkinson's disease, dystonia, or epilepsy by electrically stimulating the nerve system with a chronically transplanted electrode.

However, since such a method needs excising the deep part of the brain and transplanting an electrode, there is a problem that numerous side effects such as neuronal death, glial network disruption, and stroke may be induced during the course of operation.

Various alternative measures including optogenetic, magnetothermal, and magnetoelectric stimulators have been suggested; however, non-specific gene insertion and thermal damage to non-specific tissues are important problems that need to be solved.

Therefore, there has long been a demand for an on-demand, non-invasive, and wireless neural stimulation strategy for clinical treatment of neurodegenerative diseases.

SUMMARY OF THE INVENTION

An object of the present invention is to provide a method for increasing the blood-brain barrier permeability by opening the blood-brain barrier using a nitric oxide donor-carrying nanogenerator and a triggering stimulus to be applied thereto, and allowing a desired substance to be accumulated in the deep part of the brain.

Furthermore, it is an object of the invention to provide a method for increasing the blood-brain barrier permeability, which can alleviate degenerative brain disease symptoms, by delivering a triggering stimulus to a nanogenerator that has been delivered to the deep part of the brain and opening the $Ca^{2+}$ influx channels of neurons (nerve cell) present around the nanogenerator through a piezoelectric effect of the nanogenerator.

In order to solve the problems described above, according to an aspect of the present invention, there is provided a method for increasing the blood-brain barrier permeability, the method including: (S1) a step of delivering a nanogenerator carrying nitric oxide (NO) donor to a site adjacent to the blood-brain barrier; (S2) a step of delivering a first triggering stimulus to the area where the nanogenerator has been delivered so as to release nitric oxide from the nanogenerator; and (S3) a step of allowing the released nitric oxide to activate matrix metallopeptidase-9 (MMP-9) and inducing the activated MMP-9 to weaken the tight junction between a cerebrovascular endothelial cell and another cerebrovascular endothelial cell.

At this time, the first triggering stimulus may be any one or more selected from the group consisting of ultrasound, light, heat, and glutathione (GSH).

Here, the ultrasound may be an ultrasound with a center frequency of 1.0 to 1.5 MHz and a duty cycle of 10% to 20%.

The nanogenerator may be a nanogenerator including barium titanate ($BaTiO_3$) particles and a polydopamine layer covering the surface of the barium titanate particles.

The nitric oxide donor may be an ultrasound-responsive nitric oxide donor.

At this time, the ultrasound-responsive nitric oxide donor may be any one selected from the group consisting of N,N'-di-sec-butyl-N,N'-dinitroso-1,4-phenylenediamine (BNN6, $C_{14}H_{22}N_4O_2$), 1,3-bis-(2,4,6-trimethylphenyl)imidazolylidene nitric oxide (IMesNO), and mixtures of these.

In the step (S1), an active agent may be delivered to a site adjacent to the blood-brain barrier together with the nanogenerator.

At this time, the active agent may be a small molecule, a protein, a polysaccharide, a nucleic acid, a lipid, or a mixture of any two or more of these.

The active agent may be a pharmaceutically active agent, a diagnostically active agent, or a combination of these.

Here, the pharmaceutically active agent may be a drug, a neurotrophic factor or a growth factor for treating any one or more diseases selected from the group consisting of a neurodegenerative disease, a neuropsychiatric disease, a brain tumor, a traumatic brain injury and a stroke.

Meanwhile, the method for increasing the blood-brain barrier permeability according to the present invention may further include: (S4) a step of allowing the nanogenerator to be delivered to the deep part of the brain by passing through between a cerebrovascular endothelial cell and a cerebrovascular endothelial cell, the step being performed after the step (S3); and (S5) a step of delivering a second triggering stimulus to the nanogenerator that has been delivered to the deep part of the brain, so as to open the $Ca^{2+}$ influx channels of neurons present around the nanogenerator through a piezoelectric effect of the nanogenerator.

At this time, the second triggering stimulus may be any one or more selected from the group consisting of ultrasound, sound, mechanical pressure, and resonance.

Furthermore, the method for increasing the blood-brain barrier permeability may be used for alleviating a degenerative brain disease.

According to the method for increasing the blood-brain barrier permeability of the present invention, the blood-brain barrier can be opened by using a nitric oxide donor-carrying nanogenerator and a triggering stimulus to be applied thereto, and thus a desired substance can be accumulated in the deep part of the brain.

As a result, the accumulated substance can be used as a drug, a neurotrophic factor or a growth factor for treating a disease such as a neurodegenerative disease, a neuropsychiatric disease, a brain tumor, a traumatic brain injury, a stroke or etc.

Furthermore, when the triggering stimulus is delivered to the nanogenerator that has been delivered to the deep part of the brain, and the $Ca^{2+}$ influx channels of neurons present around the nanogenerator are opened through a piezoelectric effect of the nanogenerator, degenerative brain disease symptoms can be alleviated.

BRIEF DESCRIPTION OF THE DRAWINGS

Specifically, FIG. 9A represents calcium influx fluorescence image of differentiated SH-SY5Y cells with Fluo-4 AM (Scale bar: 50 μm).

FIG. 9B represents quantitative analysis of intracellular calcium transient. Mean fluorescence intensity (F.I.) of individual bundle and cell body ROI was selected from Fluo-4 fluorescence image, (a.u.=arbitrary units). Data: mean±SD (n=40).

FIG. 9C represents quantitative analysis of dopamine released from differentiated SH-SY5Y cells. Data: mean±SD (n=3), # compared with the control groups and evaluated by one-way ANOVA, *p<0.05, p<0.01, *p<0.001.

FIG. 9D represents sequential in vitro ultrasound neural stimulation with nanogenerator.

Specifically, FIG. 12A represents overall experimental timeline for experiment.

FIG. 12B represents fear memory induction and tests in day 3 and 4.

FIG. 12C represents illustration of transcranial ultrasound deep brain stimulation of subthalamic nucleus (STN) for Parkinson's disease model mice. Insert image represents the EB accumulated brain tissue after a STN-targeted HIFU treatment.

FIG. 12D, 12E represent freezing levels during fear conditioning and the following 24 h-after fear recall test, respectively. Data: mean±SD (n=8), # compared with the control groups and evaluated by one-way ANOVA, p<0.01, *p<0.001

FIG. 12E is representative IHC image of tyrosine hydrolase (TH) in SNc.

FIG. 12F represents quantification of the number of SNc TH$^+$ neurons in the midbrain tissue slides. Data: mean±SD (n=4), # compared with the control groups and evaluated by one-way ANOVA, p<0.01, *p<0.001.

DETAILED DESCRIPTION

Hereinafter, embodiments of the present invention will be described in detail with reference to the attached drawings so that those ordinarily skilled in the art to which the present invention is pertained can easily carry out the invention. However, the present invention can be embodied in various different forms and is not intended to be limited to the embodiments and drawings described herein.

Figure 1A:
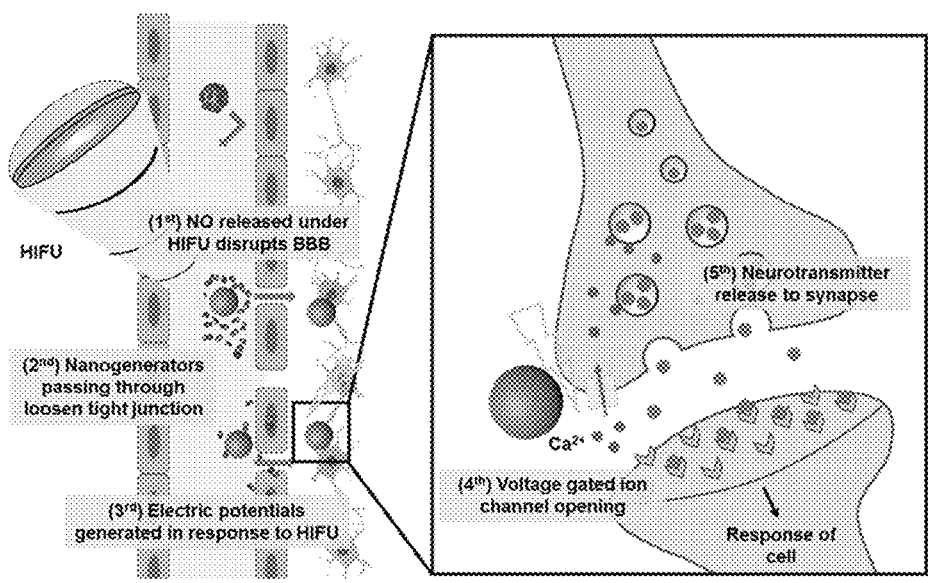
FIGS. 1A and 1B are diagrams illustrating the state in which nanogenerators according to an embodiment of the present invention act on the blood-brain barrier through ultrasound irradiation, and a process of preparing a nanogenerator.

FIG. 1 is diagrams illustrating the state in which nanogenerators according to an embodiment of the present invention act on the blood-brain barrier through ultrasound irradiation, and a process of preparing a nanogenerator.

According to FIG. 1, the method for increasing the blood-brain barrier permeability according to an embodiment of the present invention includes: (S1) a step of delivering a nanogenerator carrying a nitric oxide (NO) donor to a site adjacent to the blood-brain barrier; (S2) a step of delivering a first triggering stimulus to the area where the nanogenerator has been delivered so as to release nitric oxide from the nanogenerator; and (S3) a step of allowing the released nitric oxide to activate matrix metallopeptidase-9 (MMP-9) and inducing the activated MMP-9 to weaken the tight junction between a cerebrovascular endothelial cell and another cerebrovascular endothelial cell.

According to embodiments of the present invention, by using a nanogenerator carrying a nitric oxide donor that includes nitric oxide (NO), which is a vasodilating gas, and a triggering stimulus to be applied thereto in order to activate MMP-9 (matrix metallopeptidase-9) with released nitric oxide, and weakening the tight function between a cerebrovascular endothelial cell and another cerebrovascular endothelial cell by the activated MMP-9, the blood-brain barrier can be opened, and a desired substance can be accumulated in the deep part of the brain. As a result, the accumulated substance can be used as a drug, a neurotrophic factor or a growth factor for treating a disease such as a neurodegenerative disease, a neuropsychiatric disease, a brain tumor, a traumatic brain injury, a stroke or etc.

At this time, the first triggering stimulus may be not only ultrasound but also any one or more selected from the group consisting of light, heat, and glutathione (GSH), and the first triggering stimulus is preferably ultrasound, and more preferably high-intensity focused ultrasound (HIFU).

The ultrasound may be an ultrasound with a center frequency of 1.0 to 1.5 MHz and a duty cycle of 10% to 20%. When the ranges of the center frequency and the duty cycle are less than the above-described value ranges, the nitric oxide release amount is not sufficient, and opening of the blood-brain barrier (BBB) may be limited. When the above-described ranges exceed the value ranges, there is a problem that hyperthermal damage caused by tissue burning and permanent BBB disruption may occur.

More specifically, the center frequency may be 1.5 MHz, the power may be 462.4 W/cm$^2$, the duty cycle may be 10%, the exposure time may be 60 seconds, and the pulse repetition frequency may be 10 Hz.

The nanogenerator may be a nanogenerator including barium titanate (BaTiO$_3$) particles and a polydopamine layer covering the surface of the barium titanate particles.

On the surface of the nanogenerator, a nitric oxide donor is supported, and later, detachment of nitric oxide from the nitric oxide donor can be achieved by the ultrasound delivered to the nanogenerator.

The nitric oxide donor is not particularly limited so long as it responds to the first triggering stimulus, and preferably, any ultrasound-responsive nitric oxide donor can all be used. The nitric oxide donor may be used as a permeation enhancer for enhancing the permeability of the inner wall of the brain blood vessels. Furthermore, the nitric oxide donor may be included in an amount effective for enhancing the permeability of the inner wall of the brain blood vessels.

The ultrasound-responsive nitric oxide donor may be more specifically any one selected from the group consisting of N,N'-di-sec-butyl-N,N'-dinitroso-1,4-phenylenediamine (BNN6, C$_{14}$H$_{22}$N$_4$O$_2$), 1,3-bis-(2,4,6-trimethylphenyl)imidazolylidene nitric oxide (IMesNO), and a mixture of these; however, the nitric oxide donor is not limited to these.

The following chemical reaction scheme discloses a method for synthesizing BNN6, which is an example of the ultrasound-responsive nitric oxide donor.

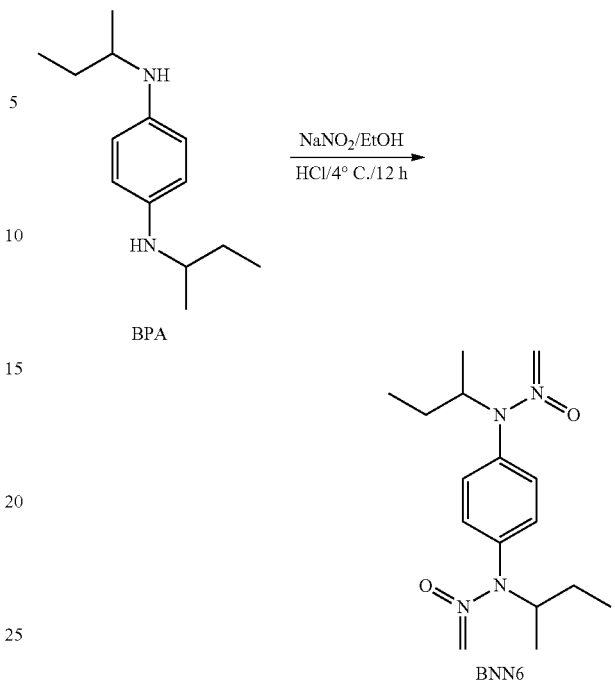

Meanwhile, in the step (S1), an active agent may be delivered together with the nanogenerator to a site adjacent to the blood-brain barrier.

In a case in which the nitric oxide donor is used in combination with the active agent, the nanogenerator may be administered according to the regimen of administration, for example, the duration of administration, of the active agent.

The brain blood vessels may be blood vessels that have strong tight junctions between vascular endothelial cells and vascular endothelial cells and do not allow or only partially allow substances to pass through the blood vessels. The above-mentioned blood vessels may form the blood-brain barrier (BBB).

The active agent may be a substance that is known to be unable to permeate, or is actually unable to permeate, through the inner membrane of the brain blood vessels. Furthermore, the active agent may be a substance that permeates through the inner membrane of the brain blood vessels only in a small amount and cannot be delivered in an effective amount in the absence of other permeation auxiliary agents.

The active agent may be a small molecule, a protein, a polysaccharide, a nucleic acid, a lipid, or a combination of these. The small molecule may be a non-polymer molecule. The molecule may be an organic compound molecule. The protein may be or may not be glycosylated. A glycoprotein may be, for example, erythropoietin (EPO). The protein may be a protein having a molecular weight of 500 Da to 1000 kDa, 500 Da to 500 kDa, 500 Da to 100 kDa, 500 Da to 500 kDa, 1 kDa to 500 kDa, 5 kDa to 500 kDa, 10 kDa to 500 kDa, or 20 kDa to 500 kDa. The polysaccharide may be dextran or starch. The nucleic acid may be a single-stranded or double-stranded polynucleotide. The nucleic acid may be siRNA, shRNA, miRNA, or an antisense oligonucleotide.

The nitric oxide donor-carrying nanogenerator and the active agent may be administered simultaneously or separately. The nanogenerator and the active agent may be administered as a single composition. This administration may be conducted such that the nanogenerator is administered first, followed by administration of the active agent. In this case, the active agent may be administered within 30 minutes, within 20 minutes, within 15 minutes, within 10 minutes, or within 5 minutes, after the administration of the nanogenerator. The active agent may be administered, for example, within 1 minute to 30 minutes, within 1 minute to 20 minutes, within 1 minute to 5 minutes, within 5 minutes to 15 minutes, within 5 minutes to 10 minutes, or within 3 minutes to 15 minutes, after the administration of the nanogenerator. The administration may be conducted such that the active agent is administered first, followed by administration of the nanogenerator. In this case, the nanogenerator may be administered within 30 minutes, within 20 minutes, within 15 minutes, within 10 minutes, or within 5 minutes, after the administration of the active agent. The nanogenerator may be administered within 1 minute to 30 minutes, within 1 minute to 20 minutes, within 1 minute to 5 minutes, within 5 minutes to 15 minutes, within 5 minutes to 10 minutes, or within 3 minutes to 15 minutes, after the administration of the active agent.

The active agent may be a pharmaceutically active agent, a diagnostically active agent, or a combination of these.

At this time, the pharmaceutically active agent may be a drug, a neurotrophic factor or a growth factor for treating any one disease selected from the group consisting of a neurodegenerative disease, a neuropsychiatric disease, a brain tumor, a traumatic brain injury and a stroke.

Meanwhile, the method for increasing the blood-brain barrier permeability according to the present invention may further include: (S4) a step of allowing the nanogenerator to be delivered to the deep part of the brain by passing through between a cerebrovascular endothelial cell and a cerebrovascular endothelial cell, the step being performed after the step (S3); and (S5) a step of delivering a second triggering stimulus to the nanogenerator that has been delivered to the deep part of the brain, so as to open the $Ca^{2+}$ influx channels of neurons present around the nanogenerator through a piezoelectric effect of the nanogenerator.

At this time, the second triggering stimulus may be any one or more selected from the group consisting of ultrasound, sound, mechanical pressure, and resonance such as resonant frequency, and the second triggering stimulus may be preferably ultrasound, and more preferably high-intensity focused ultrasound (HIFU).

Here, the nitric oxide donor carried by the piezoelectric nanogenerator may be explained as a non-invasive wireless neural stimulator.

A piezoelectric material may be mechanically deformed and polarized in order to produce a direct current output under an external stimulation. At this time, the external stimulation may be preferably high-intensity focused ultrasound (HIFU) having deep penetrability and site-specificity.

As described above, nitric oxide that has been released due to a triggering stimulus (ultrasound or the like) temporarily induces destruction of the blood-brain barrier, and the systemically administered nanogenerator reaches to the deep part of the brain, electrically stimulates dopaminergic nerve in the living body, and induces fear memory against the triggering stimulus (ultrasound or the like). Ultimately, when the nanogenerator according to the present invention and a triggering stimulus (ultrasound or the like) to be applied thereto are used, non-invasive deep brain stimulation (DBS) can be achieved.

According to another aspect of the present invention, there is provided a method for delivering an active agent to an individual, the method including a step of administering a nitric oxide-carrying nanogenerator and the active agent to the individual.

With regard to the above-described method, the nanogenerator and the active agent are as described above.

The administration may be performed by methods that are known in the pertinent art. Regarding the administration, the nitric oxide-carrying nanogenerator and the active agent can be directly administered to an individual by any means through a route such as, for example, intravenous, intramuscular, oral, transdermal, transmucosal, intranasal, intratracheal, or subcutaneous administration. This administration may be conducted systemically or topically. The administration may involve applying the agents in a localized manner to a BBB site, for example, the brain, spinal cord, or retina.

The individual may be a mammal, for example, a human being, a cow, a horse, a pig, a dog, a sheep, a goat, or a cat. The individual may be an individual having a disease in the brain, spinal cord, or retina.

The administration may be conducted by administering a nanogenerator and an active agent respectively in an amount of 0.01 mg to 1,000 mg, for example, 0.1 mg to 500 mg, 0.1 mg to 100 mg, 0.1 mg to 50 mg, 0.1 mg to 25 mg, 1 mg to 1,000 mg, 1 mg to 500 mg, 1 mg to 100 mg, 1 mg to 50 mg, 1 mg to 25 mg, 5 mg to 1,000 mg, 5 mg to 500 mg, 5 mg to 100 mg, 5 mg to 50 mg, 5 mg to 25 mg, 10 mg to 1,000 mg, 10 mg to 500 mg, 10 mg to 100 mg, 10 mg to 50 mg, or 10 mg to 25 mg, per day for each individual.

The nanogenerator and the active agent may be administered simultaneously or separately. The nanogenerator and the active agent may be administered as a single composition or as separate compositions. The administration may be performed such that the nanogenerator is administered first, followed by administration of the active agent. In this case, the active agent may be administered within 30 minutes, within 20 minutes, within 15 minutes, within 10 minutes, or within 5 minutes, after the administration of the nanogenerator. The active agent may be administered, for example, within 1 minute to 30 minutes, within 1 minute to 20 minutes, within 1 minute to 5 minutes, within 5 minutes to 15 minutes, within 5 minutes to 10 minutes, or within 3 minutes to 15 minutes, after the administration of the nanogenerator. The administration may be conducted such that the active agent is administered first, followed by administration of the nanogenerator. In this case, the nanogenerator may be administered within 30 minutes, within 20 minutes, within 15 minutes, within 10 minutes, or within 5 minutes, after the administration of the active agent. The nanogenerator may be administered, for example, within 1 minute to 30 minutes, within 1 minute to 20 minutes, within 1 minute to 5 minutes, within 5 minutes to 15 minutes, within 5 minutes to 10 minutes, or within 3 minutes to 15 minutes, after the administration of the active agent.

The above-described method may be intended to diagnose the presence of a substance or a symptom, or to treat a symptom. The substance or symptom may be present in the brain, the retina, or the spinal cord.

The active agent may be a pharmaceutically active agent or a diagnostically active agent. The method may include administering a pharmaceutically or diagnostically acceptable carrier together.

The nitric oxide donor-carrying nanogenerator may be administered in an amount effective for enhancing the permeability of the blood-brain barrier.

According to another aspect of the present invention, there is provided a use of a nitric oxide donor-carrying nanogenerator for being used in a method for delivering an active agent to an individual. This use may be intended to deliver an active agent to an individual through the brain blood vessels.

Hereinafter, the present invention will be described in more detail by way of specific Examples. The following Examples are only for the purpose of illustrating the present invention and describe only that ultrasound is used as the first and second triggering stimuli. However, as described above, the first triggering stimulus can be light, heat, glutathione (GSH) or the like in addition to ultrasound, while the second triggering stimulus can be sound, mechanical pressure, resonance, or the like in addition to ultrasound, and the present invention is not intended to be limited by the following Examples.

1. Production of Ultrasound-Responsive Nanogenerator

The precondition for an on-demand, non-invasive wireless neuronal stimulator is that the stimulator should respond to ultrasound, preferably to HIFU (high-intensity focused ultrasound), and generate both nitric oxide and direct current output. BTNP-pDA-BNN6 that fully satisfies the above-described condition was produced by an oxidation polymerization step of gradually coating the surface of piezoelectric BTNP ($BaTiO_3$ nanoparticles) with polydopamine; and a step of loading ultrasound-responsive BNN6 on the polydopamine coating layer (see FIG. 1B).

Figure 2A:
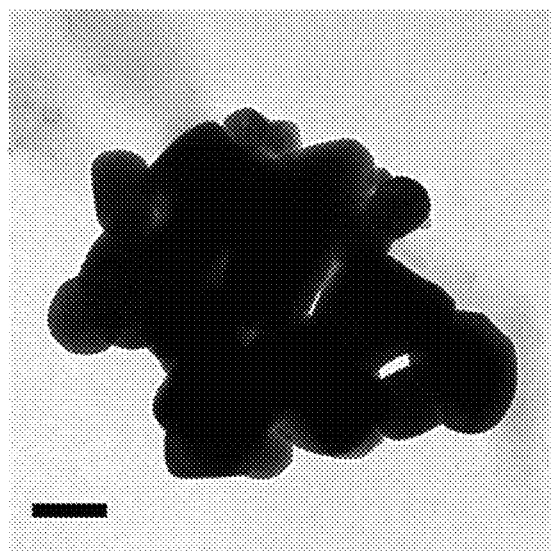
FIGS. 2A and 2B are transmission electron microscopic (TEM) photographs (scale bar, 300 nm) of (a) BTNP according to an embodiment of the present invention, and (b) BTNP-pDA including BTNP and a polydopamine layer covering the surface of BTNP.
Figure 2B:
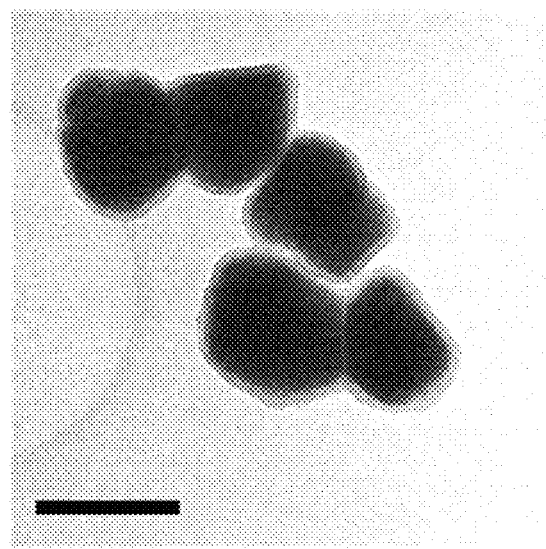

More particularly, piezoelectric BTNP having a size of 200 nm was selected as a starting substance. This BTNP exhibits high potential for producing output current inside a biological system; however, due to its hydrophobic properties, the clinical usage is limited, and the substance instantaneously aggregates under aqueous conditions (see FIG. 2A). Therefore, BTNP was coated with polydopamine (pDA), which is a biocompatible and electroconductive polymer, by oxidation polymerization in order to mitigate in vivo toxicity and hydrophobicity. The core-shell structure of polydopamine-coated BTNP-pDA was confirmed by TEM images (see FIG. 2B).

Figure 3A:
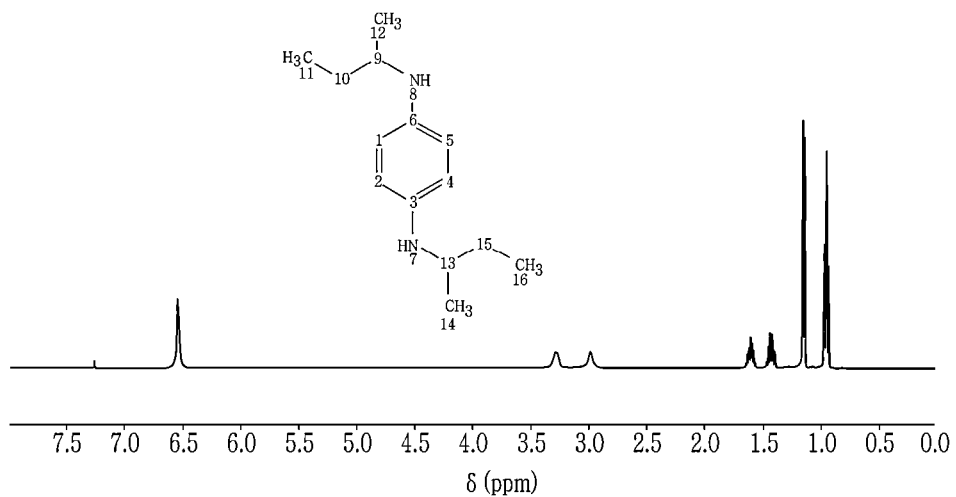
FIGS. 3A and 3B are charts showing the $^1$H-NMR spectra of (a) BPA and (b) BNN6 according to an embodiment of the present invention ($^1$H-NMR (500 MHz, CDCl$_3$), d=7.50 (s, 4H), 4.84-4.70 (m, 2H), 1.82-1.63 (m, 2H), 1.47 (d, J=6.9 Hz, 6H), 1.06 (t, J=7.4 Hz, 6H)).
Figure 3B:
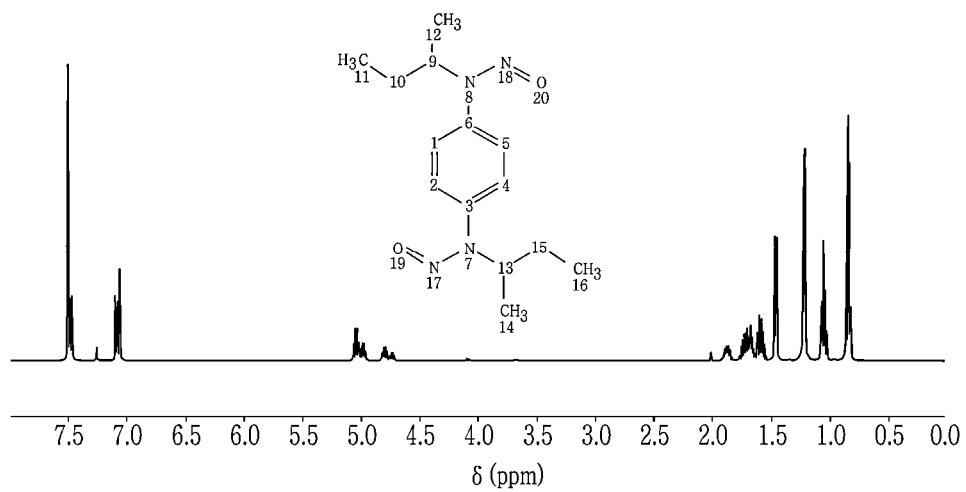

Subsequently, BNN6 as an ultrasound-responsive nitric oxide donor was prepared by synthesizing from N,N'-di-sec-butylamino-p-phenylenediamine (BPA), and synthesis of BNN6 was confirmed by $^1$H-NMR and an LC-MS (ESI$^+$) analysis. In the $^1$H-NMR spectra, the secondary amine peaks disappearing at d=2.99 and 3.29 ppm show that two NO moieties replaced two hydrogen atoms in the p-phenylene-diamine of BPA to form BNN6 (see FIGS. 3A and 3B).

Figure 4A:
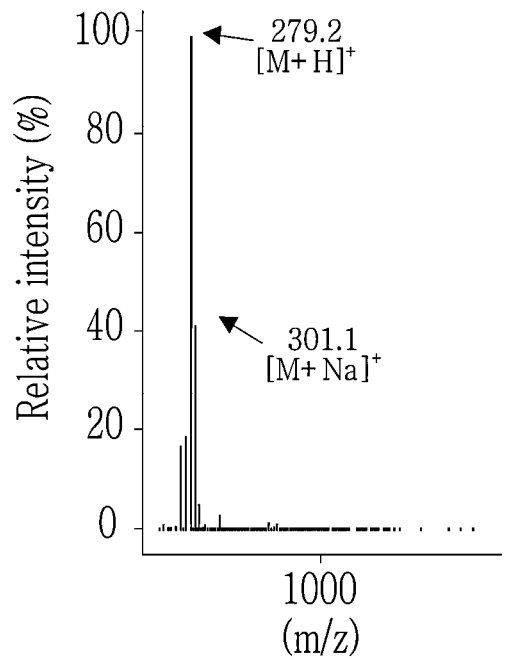
FIGS. 4A and 4B are charts showing the LC-MS (ESI$^+$) analysis data of BNN6 synthesized according to an embodiment of the present invention.
Figure 4B:
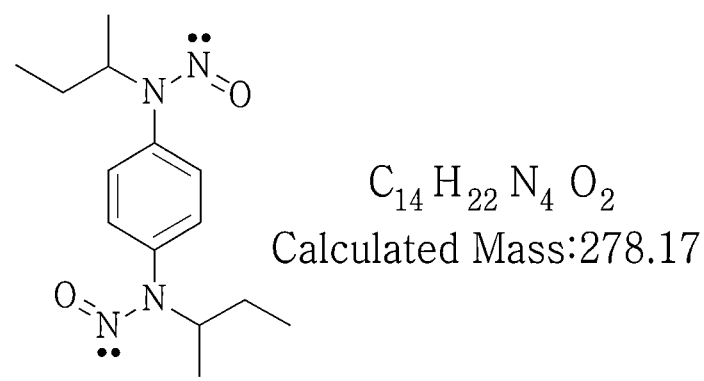
Figure 4C:
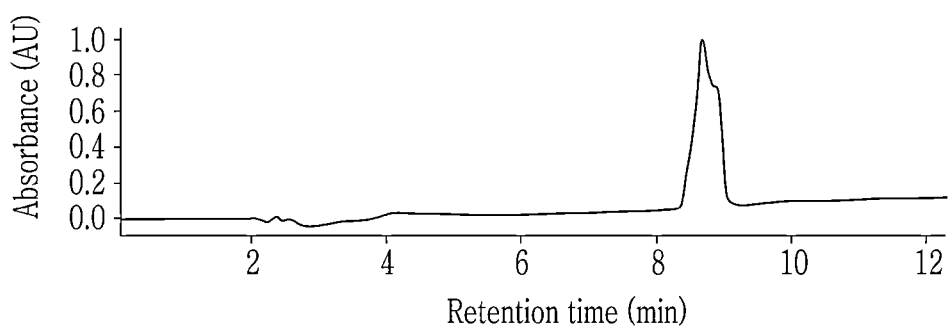
Figure 5A:
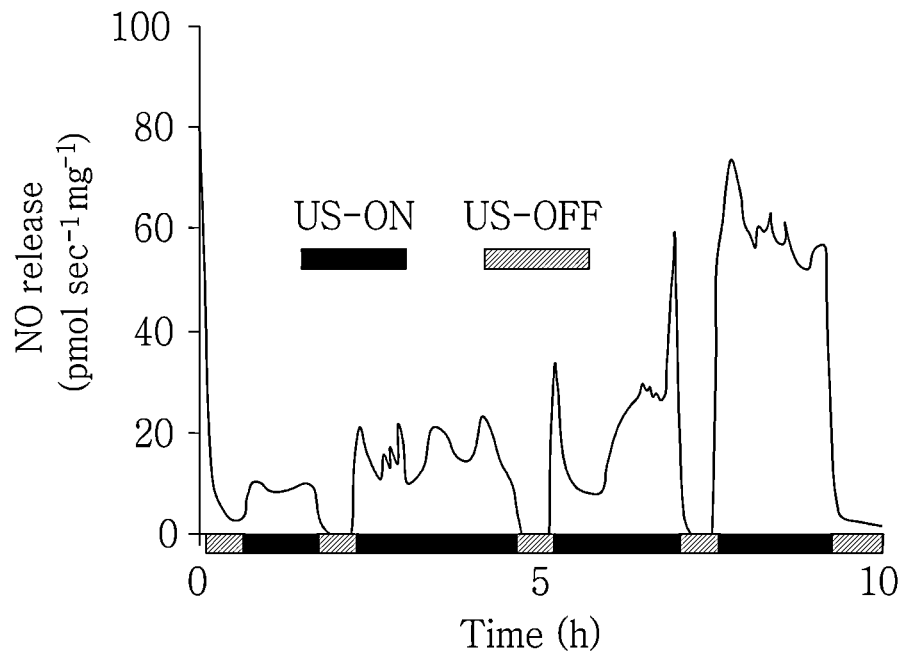
FIGS. 5A and 5B are charts showing the ultrasound-responsive NO release behavior of BNN6 according to an embodiment of the present invention.
Figure 5B:
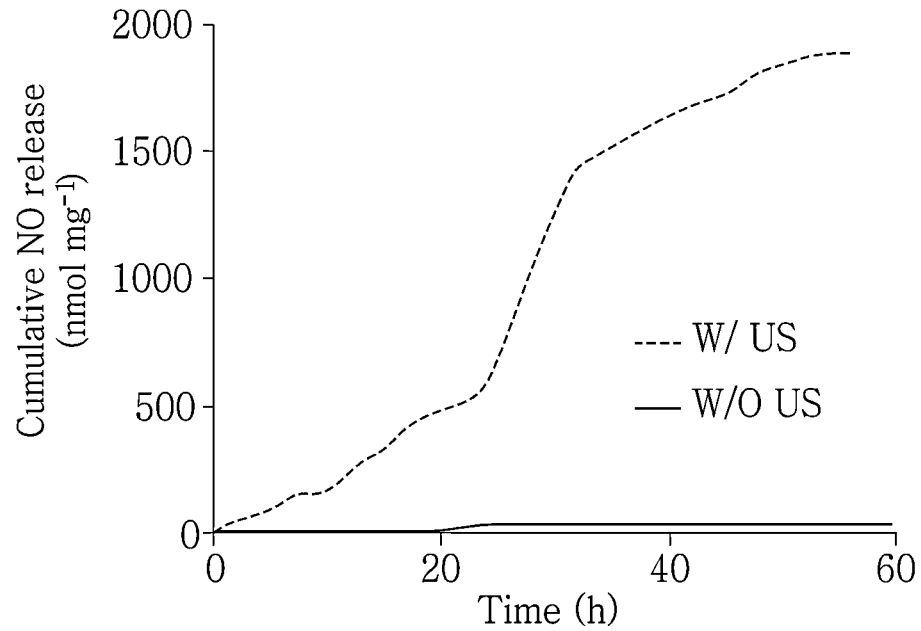

Furthermore, the LC-MS (ESI$^+$) data showed that the molecular weight of the BNN6 thus synthesized was 279 g/mol, which suggested that the molecular weight was perfectly consistent with the chemical structure (see FIG. 4). The ultrasound-responsive nitric oxide release behavior of BNN6 was examined by a real-time NO analysis, and the results showed complete NO-releasability for a target (see FIG. 5).

Figure 1B:
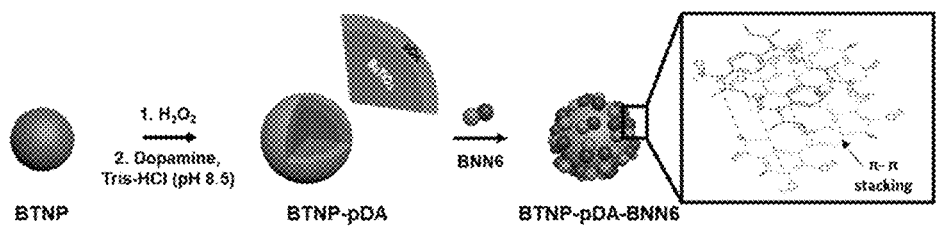
Figure 6A:
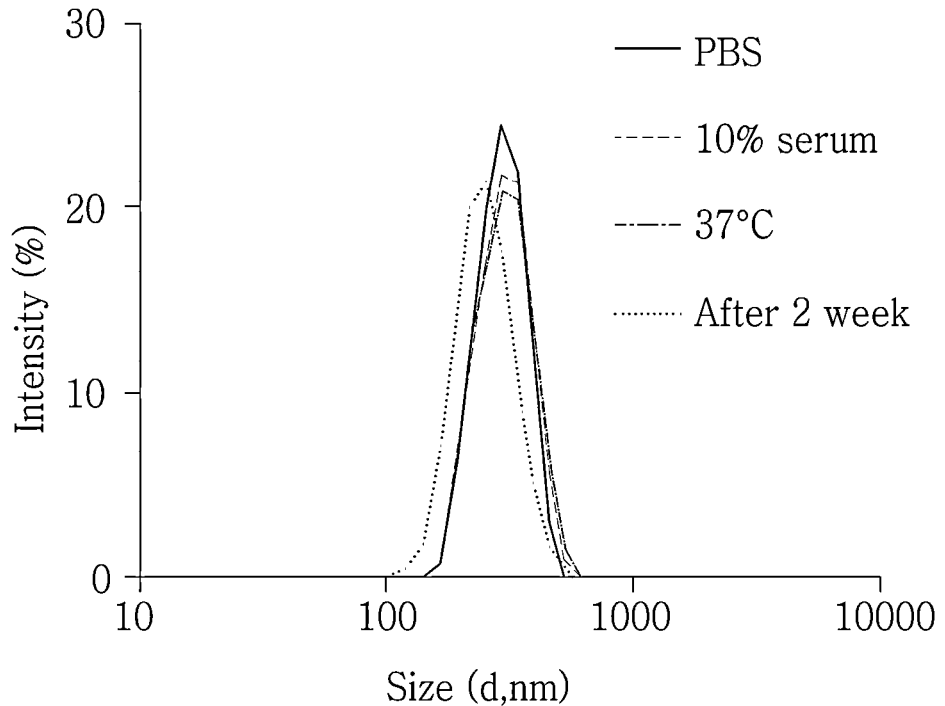
FIGS. 6A and 6B are charts showing the stability of the nanogenerator produced according to an embodiment of the present invention.
Figure 6B:
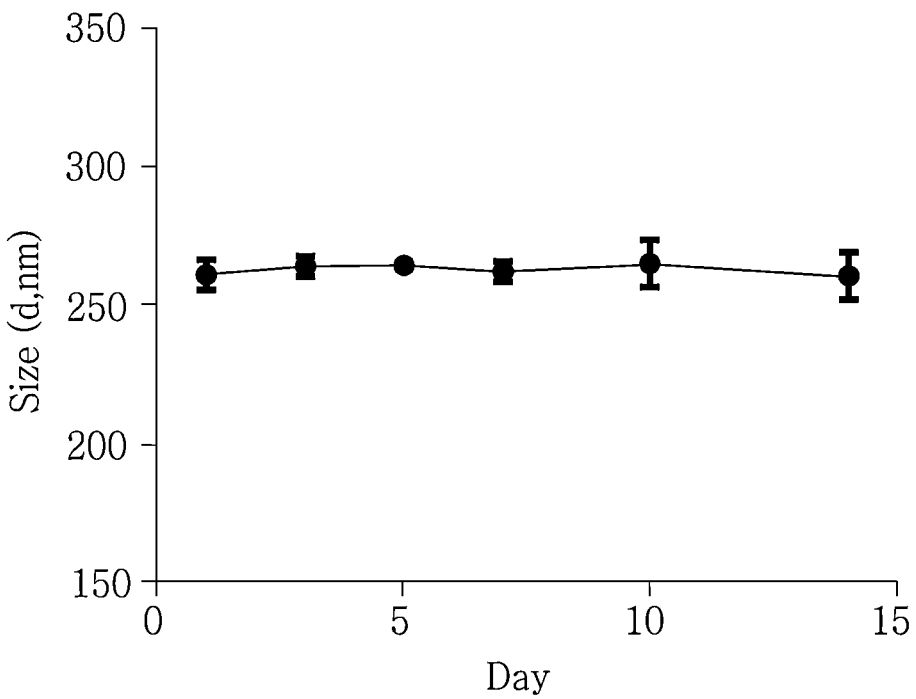

In order to complete the production of a nanogenerator, BTNP-pDA and BNN6 were incubated together in a 10 wt % acetonitrile (ACN) solution so as to load water-insoluble BNN6 on the surface of polydopamine through π-π attraction as shown in FIG. 1B. The nanogenerator had a core-shell structure as shown in FIG. 1B. The size and distribution of the nanogenerator were maintained without changing under various physiological conditions even in the presence of blood serum, which is a component that generally induces aggregation during blood circulation (see FIG. 6).

Figure 7A:
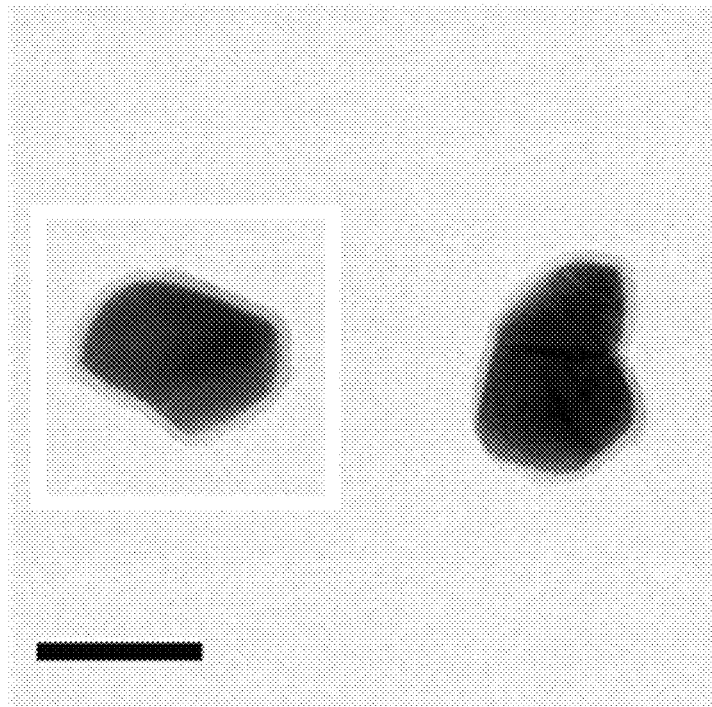
FIGS. 7A to 7I are charts showing the physical characteristics of the nanogenerator produced according to an embodiment of the present invention.
Figure 7B:
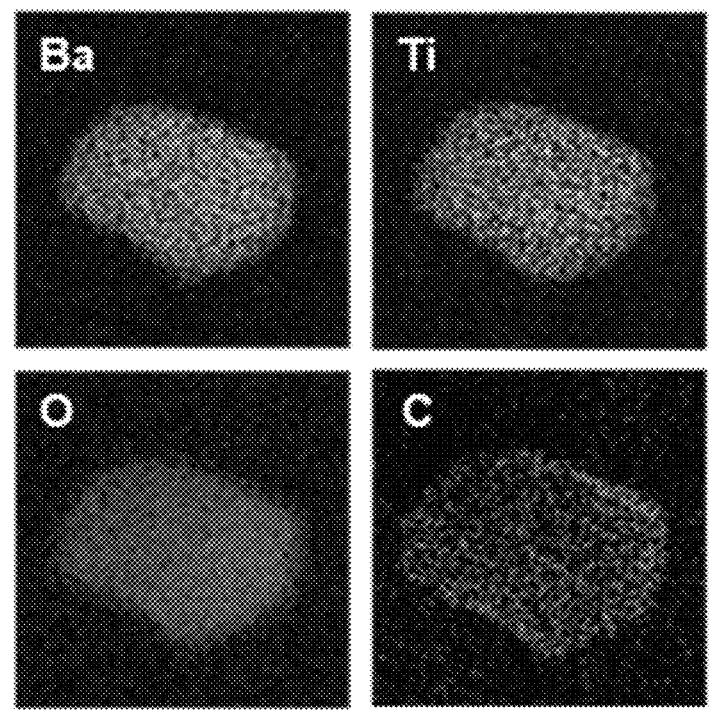
Figure 7C:
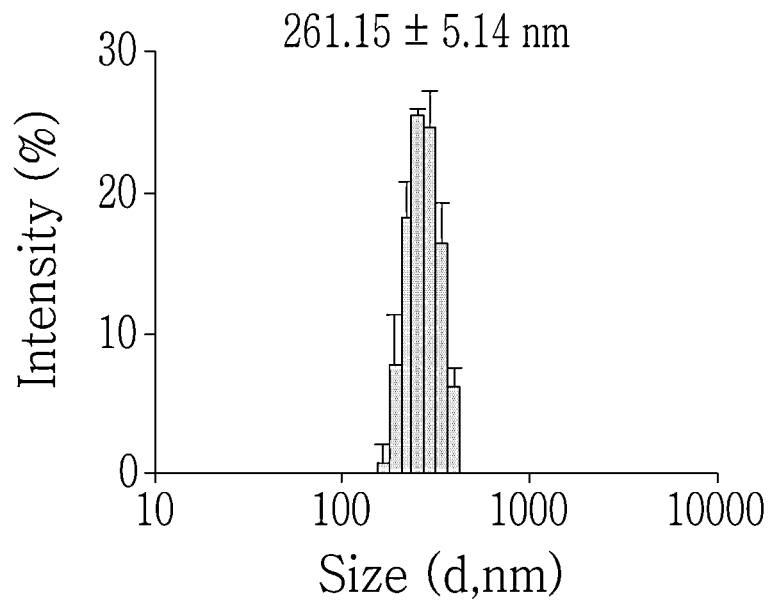
Figure 7D:
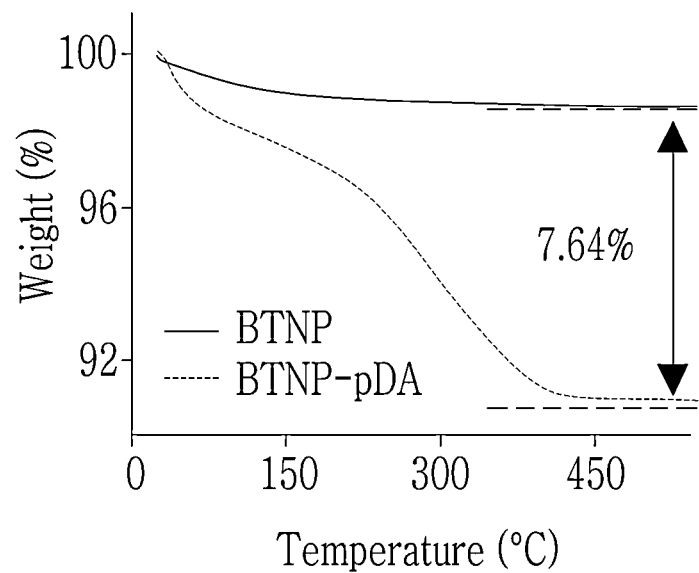
Figure 7E:
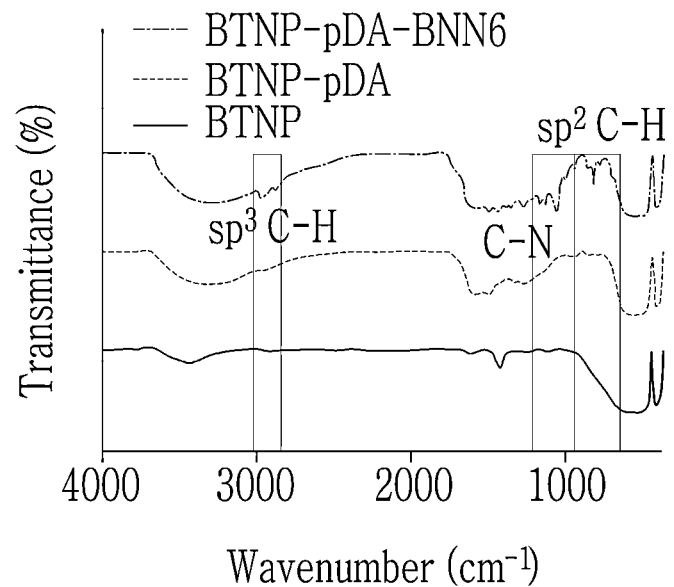
Figure 7F:
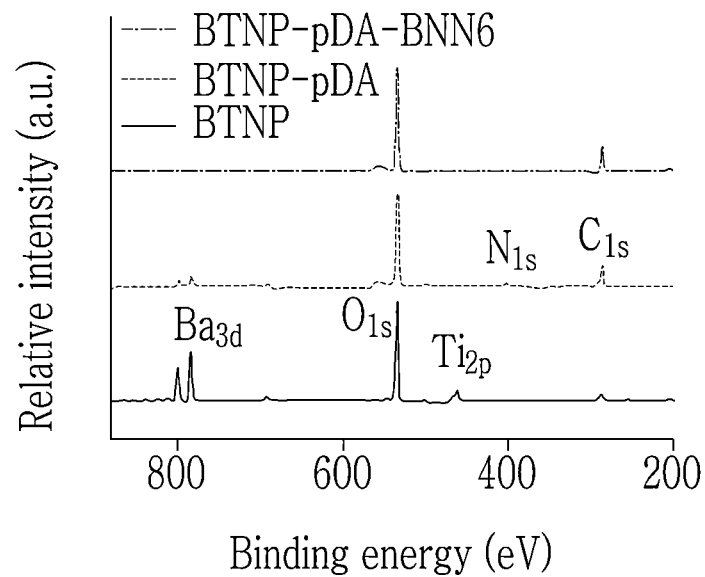
Figure 7G:
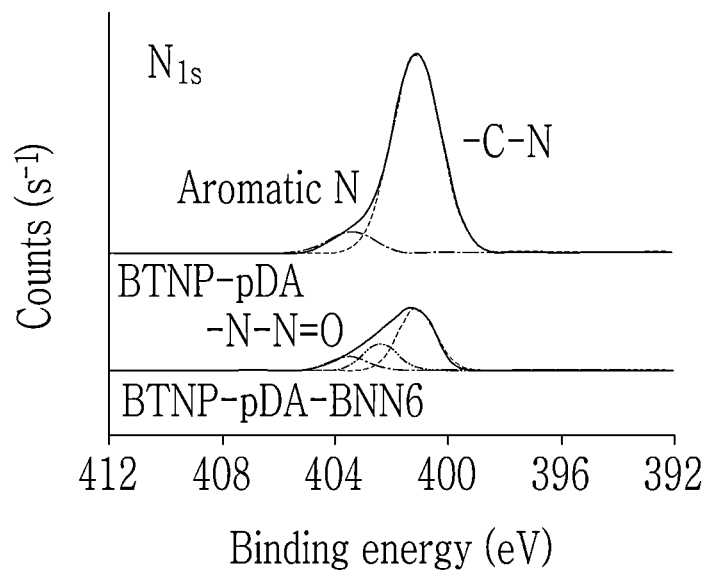
Figure 7H:
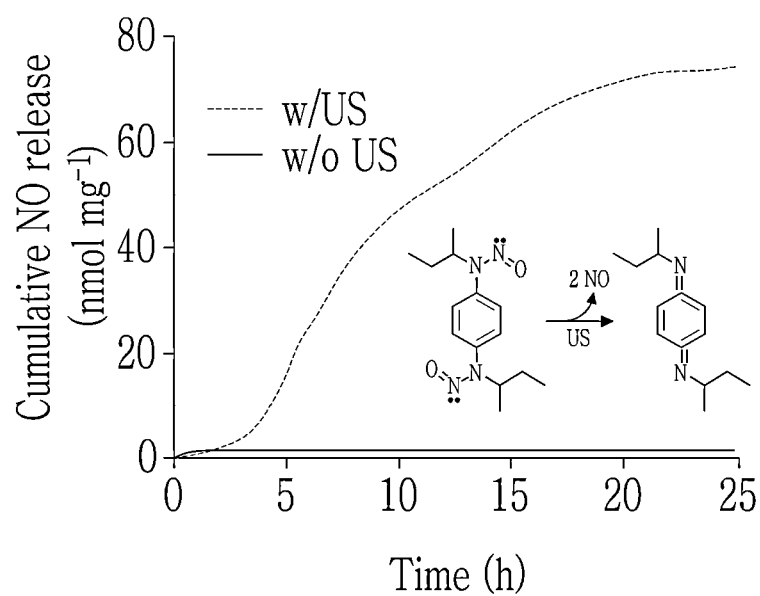

Subsequently, ultrasound-responsive NO release of the nanogenerator was monitored under physiological conditions (DPBS, pH 7.4, 37° C.). When ultrasound was absent, only a small overall amount (1.53 nmol/mg) of NO was released. In contrast, when ultrasound was irradiated, a larger overall amount of NO (74.5 nmol/mg) was released, and NO was released at a rate of 2.97 pmol/mg as the maximum instantaneous concentration per second (see FIG. 7H).

Figure 7I:
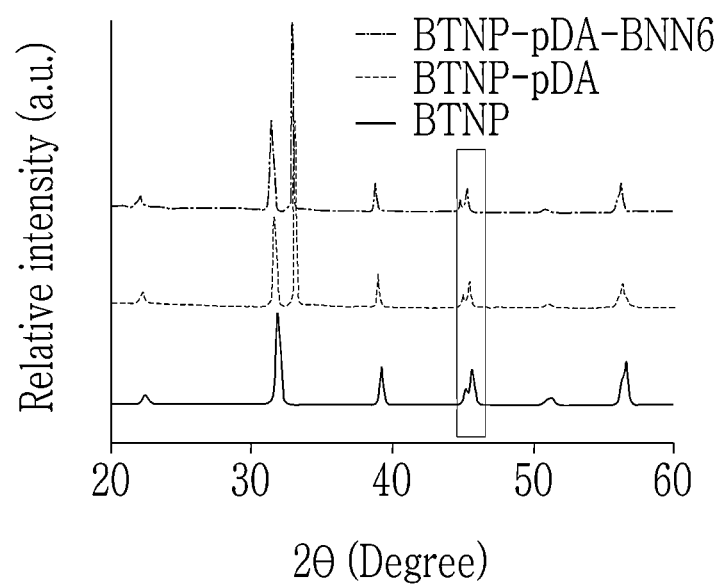

It was demonstrated that the nanogenerator produced according to the present invention maintained piezoelectric characteristics and has a potential of producing direct current output in response to ultrasound. From an X-ray diffraction (XRD) analysis, the crystallographic structure showed two different distinct peaks at 2θ≈45°, and this implies the presence of tetragonality after surface modification (see FIG. 7I).

2. Measurement of Electrochemical Behavior of Nanogenerator

Figure 8A:
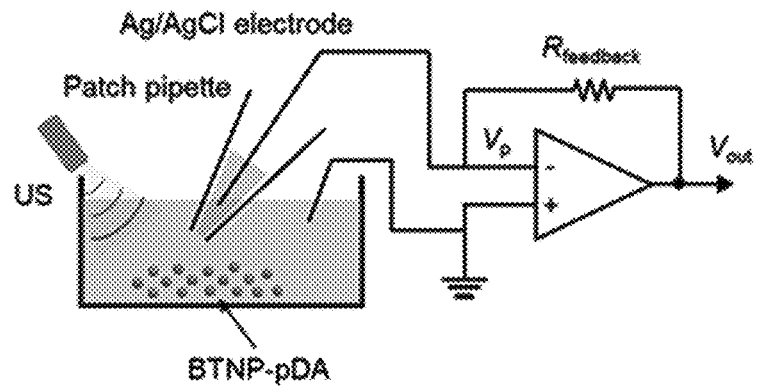
FIG. 8A is a diagram illustrating a method for measuring an electric current that is generated as the nanogenerator produced according to an embodiment of the present invention responds to ultrasound.
Figure 8B:
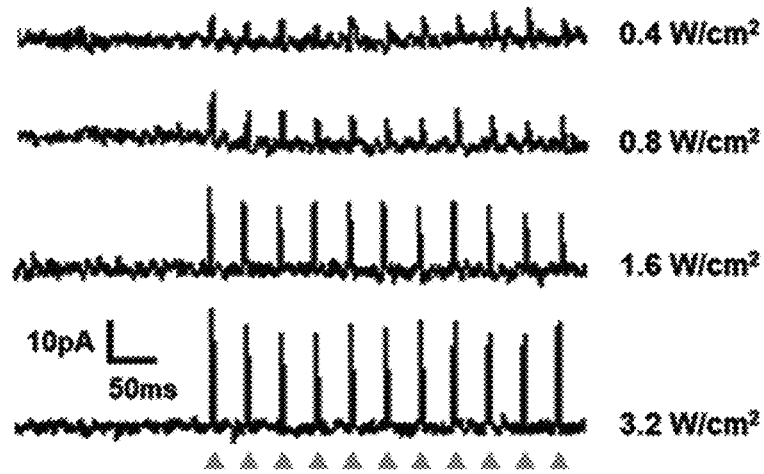
FIGS. 8B and 8C are charts showing the results.
Figure 8C:
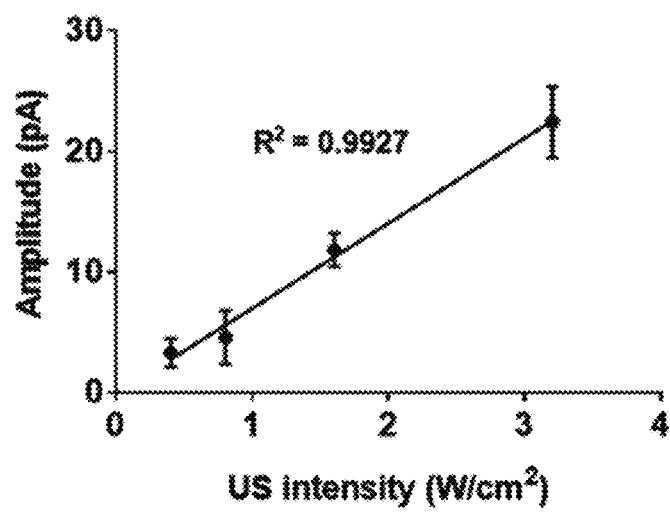

The electrochemical behavior of the nanogenerator produced as described above was investigated, and the method developed by Ramya, et al was extended. A patch-clamp provided under physiological conditions was used for recording the electric potential generated by suspended ultrasound-responsive nanogenerator (see FIG. 8A). All measurements were made in a voltage-clamp mode, and the voltage was maintained at −70 mV as virtual cellular conditions. The pipette current was measured by applying various intensities of ultrasound (see FIG. 8B). The pipette current in the presence of the nanogenerator proportionally increased to approximately ~3.30, ~4.57, ~11.8, and ~22.4 pA in response to ultrasound intensities of 0.4, 0.8, 1.6, and 3.2 W/cm$^2$, respectively (see FIG. 8C). When the nanogenerator was removed from the solution, no current was recorded. Such ultrasound-induced potential demonstrated a possibility that fine electrical nerve stimulation can be achieved.

3. Nerve Stimulation Using Nanogenerator

Figure 9A:
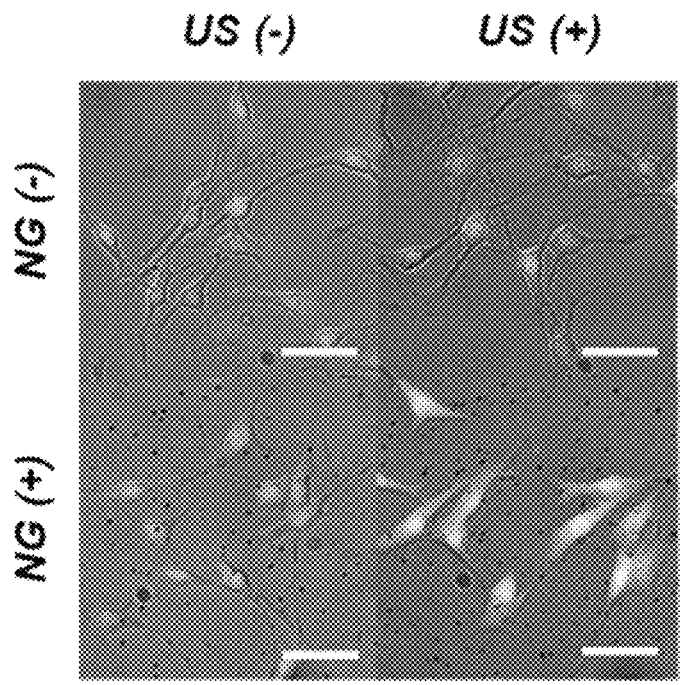
FIGS. 9A to 9D are diagrams and charts showing an in vitro ultrasound neural stimulation experiment according to an embodiment of the present invention and the results of the experiment.
Figure 9B:
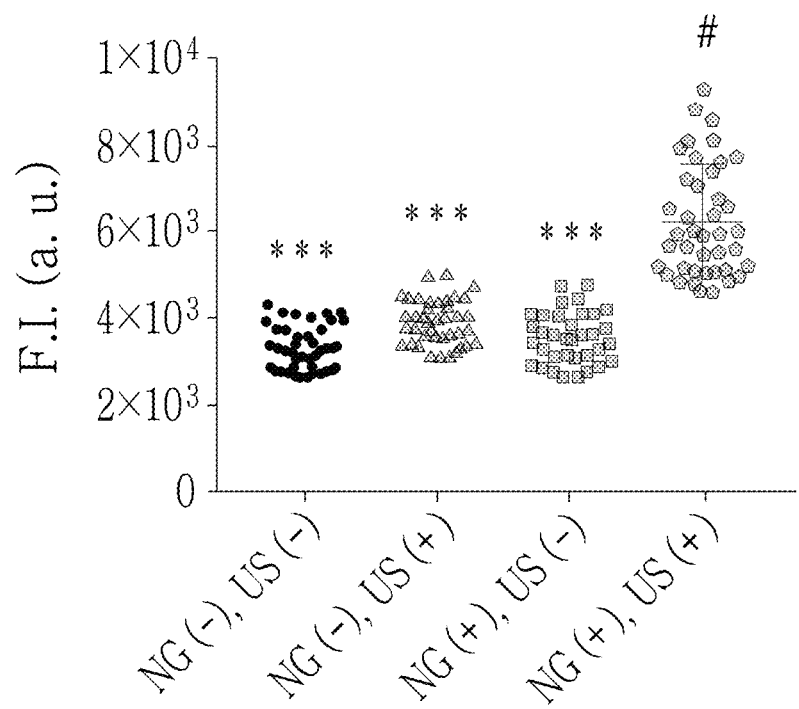

Extracorporeal ultrasound stimulation in the presence of the nanogenerator produced as described above was performed. A cytotoxicity test was performed in order to find the optimum ultrasound condition, and as a result, it was found that an ultrasound intensity higher than 0.8 W/cm$^2$ affected the viability of differentiated SH-SY5Y neurons. Therefore, the cytotoxicity test was performed while the ultrasound intensity was maintained at 0.4 W/cm$^2$ with a duty cycle of 50%. In order to investigate the extracorporeal nerve stimulation, the intracellular calcium dynamics irrespective of the presence of a nanogenerator was monitored. It was found from Fluo-4 AM fluorescence images that the nanogenerator (NG) can stimulate SH-SY5Y-derived neurons when ultrasound is applied (see FIGS. 9A and 9B). Such calcium retention with high amplitudes suggests that the electric potential generated by the nanogenerator opens voltage-gated channels and induces calcium influx.

Figure 9C:
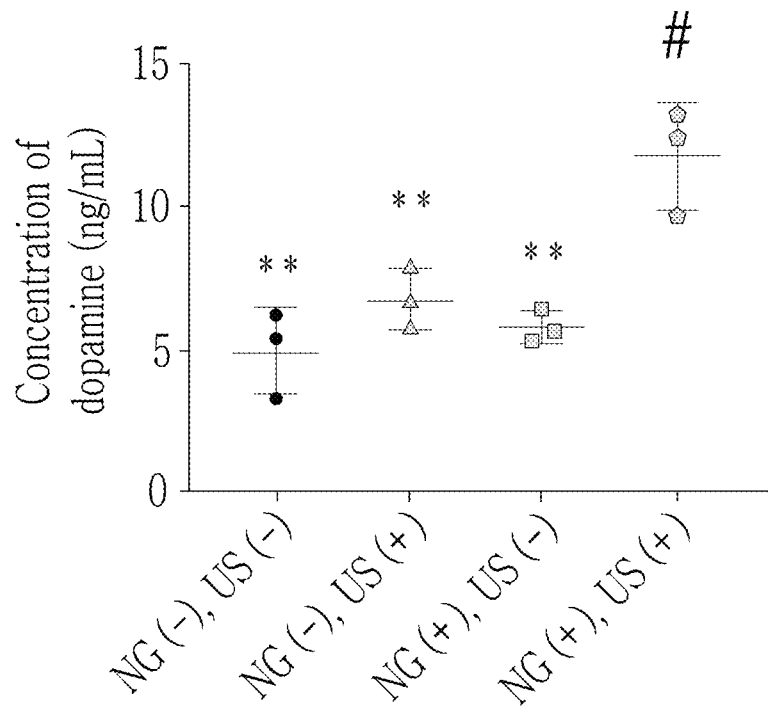
Figure 9D:
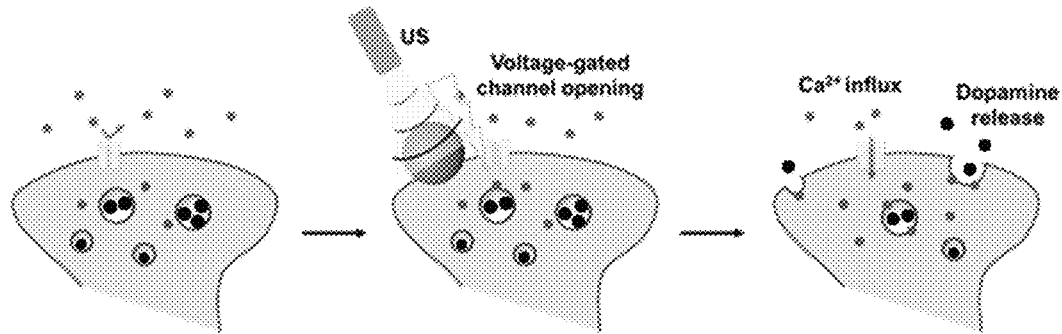

The intracellular calcium concentration plays an important role in the release of neurotransmitters and promotes gathering of ready-to-release vesicles. At the nerve endings, calcium induces release of neurotransmitters during the action potential period. An investigation was conducted to see whether the release of ultrasound-responsive neurotransmitters induced by calcium influx occurred, and after short irradiation of ultrasound, the concentration of dopamine, a neurotransmitter, in the medium was measured using ELISA. The concentration of dopamine increased significantly when the system was treated with both the nanogenerator and ultrasound, and this implies that the release of neurotransmitters from SH-SY5Y-derived dopaminergic neurons was accelerated (see FIG. 9C).

4. NO-Associated BBB Permeation of Nanogenerator

Figure 10A:
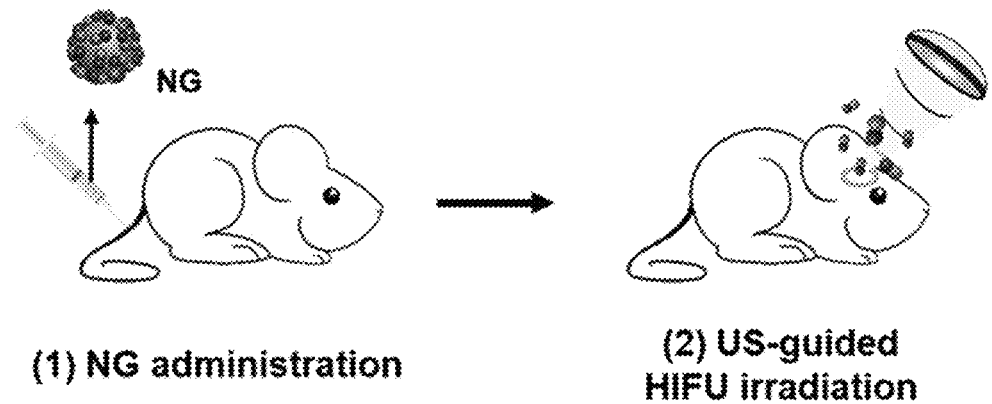
FIGS. 10A to 10G are diagrams and charts showing the course of accumulation of ultrasound-responsive nanogenerators according to an embodiment of the present invention.
Figure 10B:
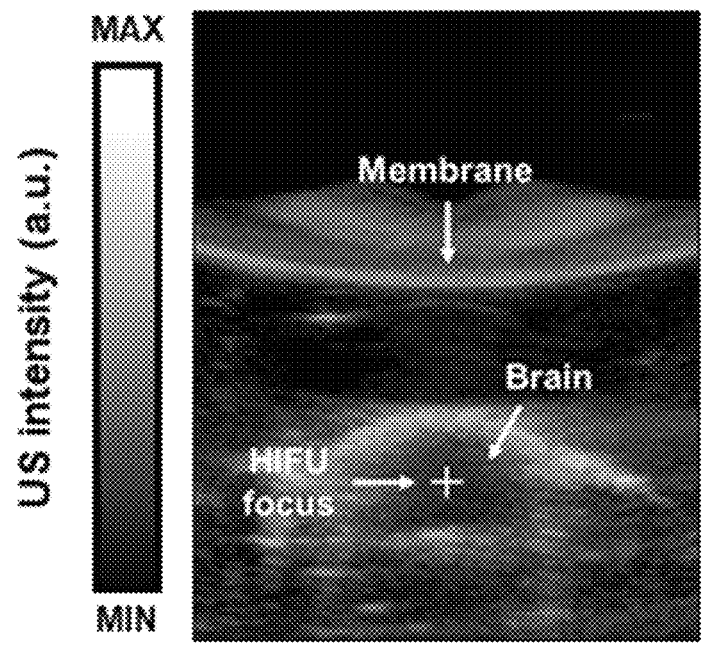

In order to evaluate the influence of NO on the BBB permeation in brain tissues, the nanogenerator in a volume of 80 mg/kg was intravenously administered to 8-week old female Balb/c mice, and then the mice were exposed to ultrasound (see FIG. 10A). Before an in vivo test, a sample was administered under preliminarily optimized conditions, and then the brains were irradiated with ultrasound.

Figure 11:
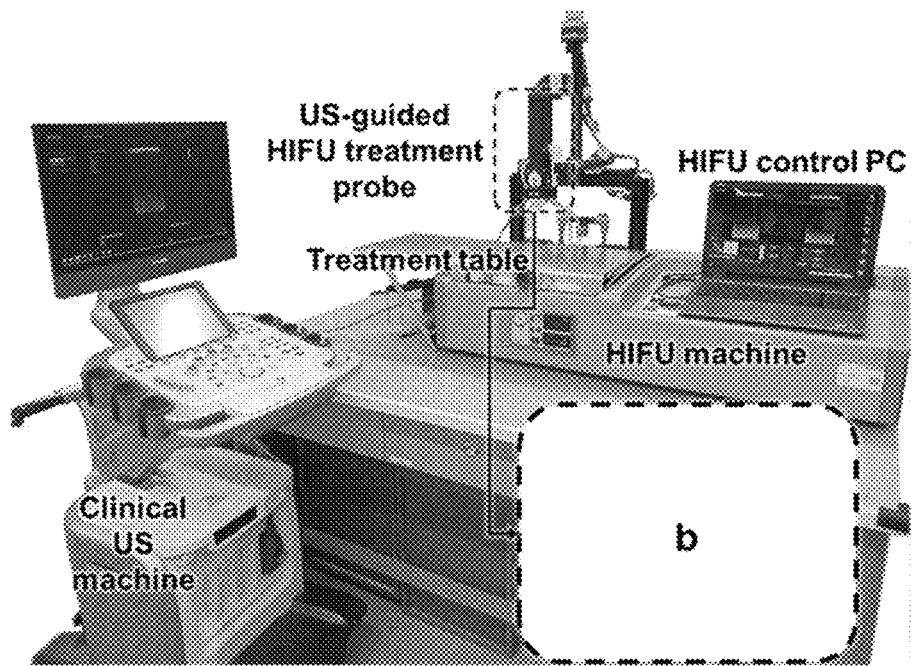
FIGS. 11A and 11B are diagrams showing an ultrasound stimulator according to an embodiment of the present invention.
Figure 11:
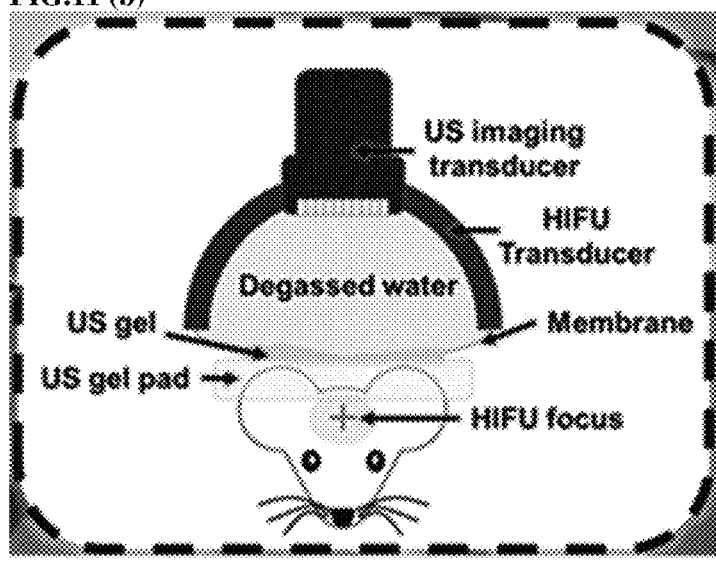

For an effective ultrasound treatment, the treated site was monitored in real time under ultrasonic guidance, using an ultrasonic imaging system-synchronized ultrasonication apparatus (see FIG. 11).

Two hours after the treatment with injection and ultrasound treatment, the mice were victimized, and then the amount of the nanogenerator accumulated inside the brain was quantified. The brain was digested with aqua regia using an ICP-OES analysis, and then the barium ion concentration inside the brain tissue was measured.

Figure 10C:
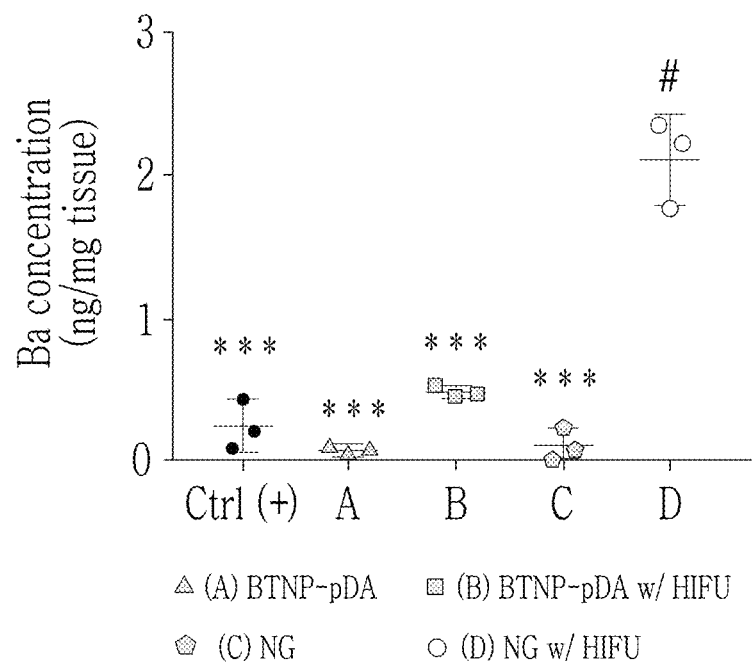
Figure 10D:
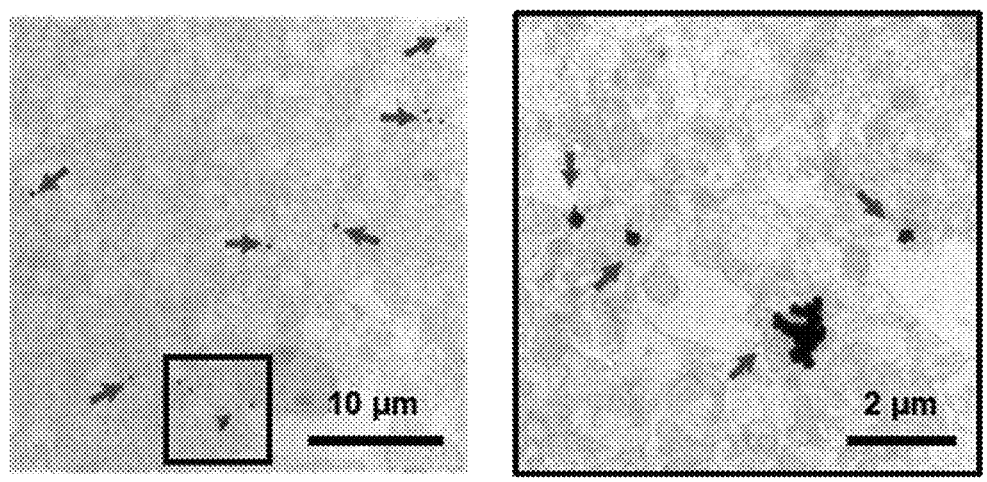

The unwanted barium ion concentration detected from the mice in a saline-treated negative control group (Ctrl (−)) was subtracted from the respective values. It was discovered that the barium ion concentration dramatically increased only in Group D, and this implies that NO had permeated through the BBB, and the nanogenerator (NG) was accumulated (see FIG. 10C). This value was about 8.2 times higher than the positive control group (Ctrl (+), diuretic mannitol at a volume of 400 mg/kg). In order to visualize accumulation of the nanogenerator inside the brain, midbrain tissue fragments of the mice in Group D were subjected to electron microscopic imaging, and thus the BBB-permeated nanogenerator could be effectively situated in the brain (see FIG. 10D).

Figure 10E:
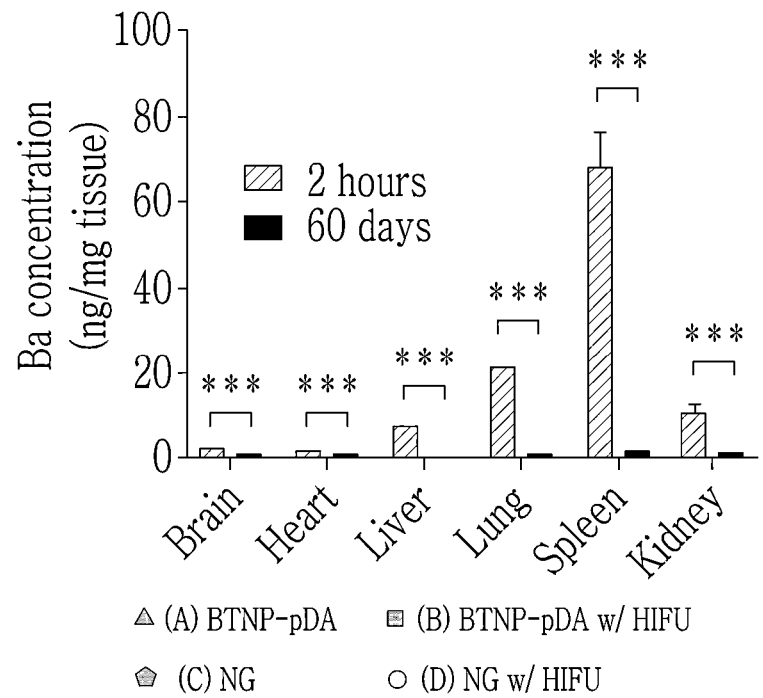
Figure 10F:
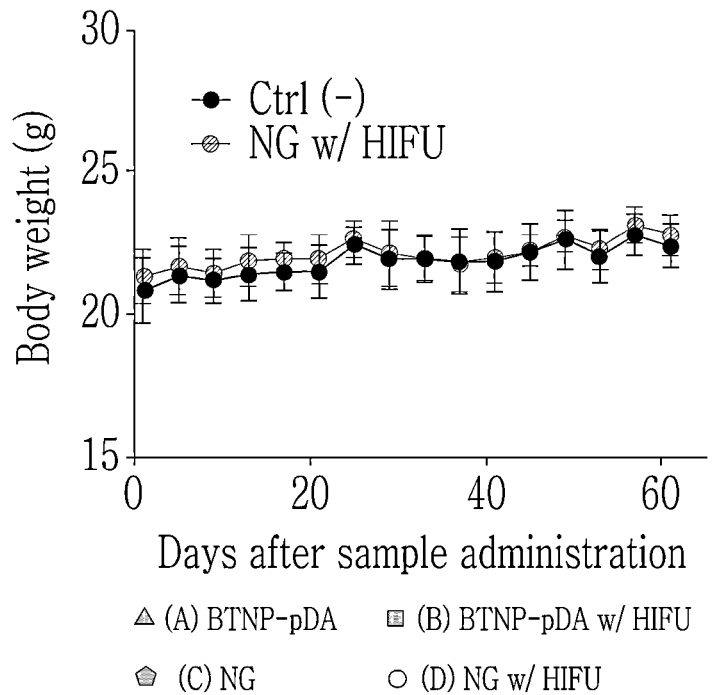
Figure 10G:
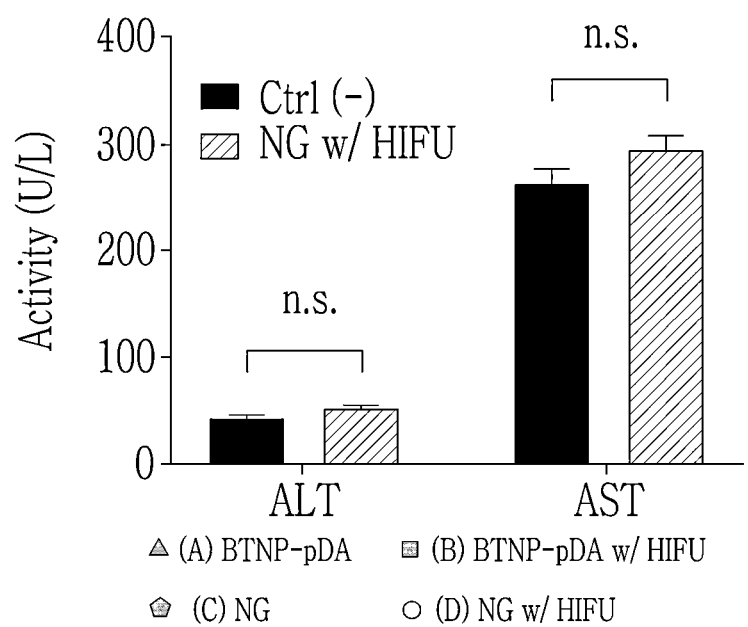

Meanwhile, the long-term in vivo removal and toxicity of the administered nanogenerator were additionally investigated. An ICP-OES analysis was conducted to measure the in vivo distribution and the in vivo residual amount of the nanogenerator. The barium ion concentrations in the brain tissue and other various tissues were noticeably reduced 60 days after the injection (see FIG. 10E). The cleaning mechanism in the brain is still not clearly understood; however, it could be confirmed that uptake and release of the cerebrospinal fluid (CSF) can be involved in the removal of the nanogenerator as in the case of the removal of other macromolecular wastes, and no unusual reduction in body weight after the sample treatment was observed (see FIG. 10F).

5. Non-Invasive Ultrasound Deep Brain Stimulation

It was checked whether the electric potential generated by the nanogenerator upon irradiation with ultrasound could stimulate neurons in the body so as to change the behavior of awake mice.

Figure 12A:
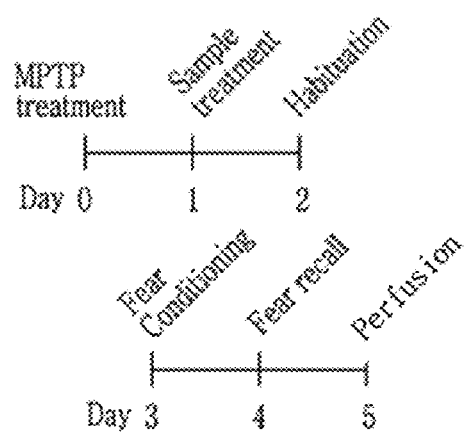
FIGS. 12A to 12G are diagrams and charts showing an in vivo ultrasound neural stimulation experiment according to an embodiment of the present invention and the results of the experiment.
Figure 12B:
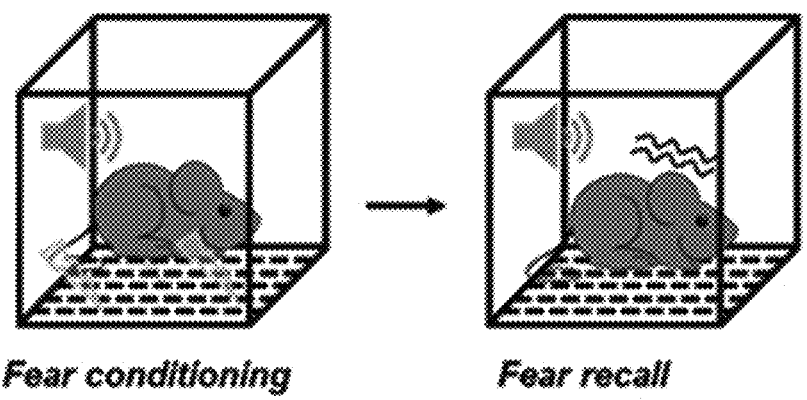
Figure 12C:
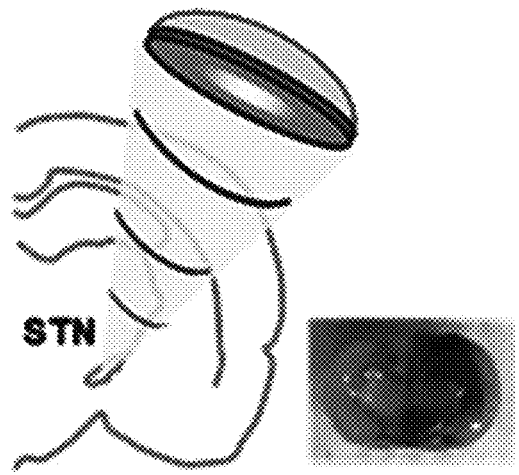
Figure 12D:
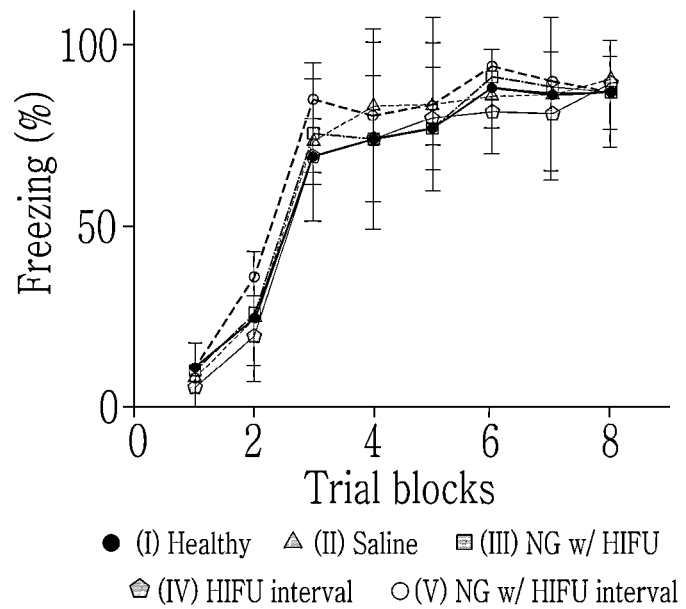
Figure 12E:
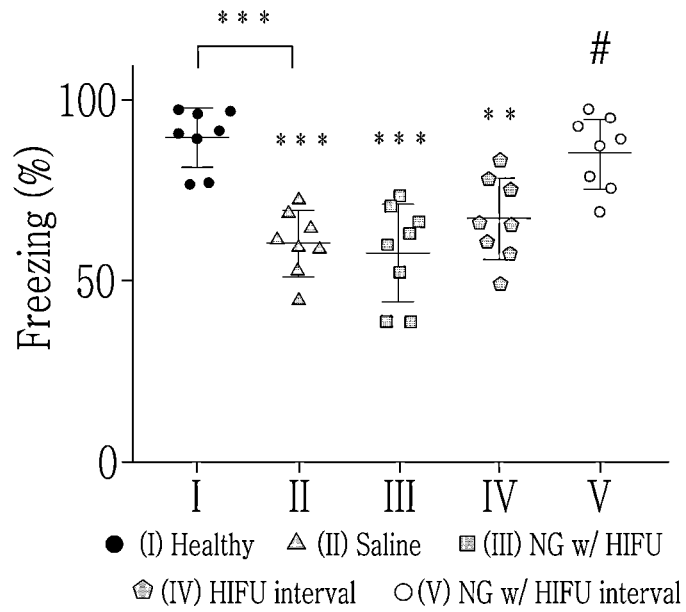
Figure 12F:
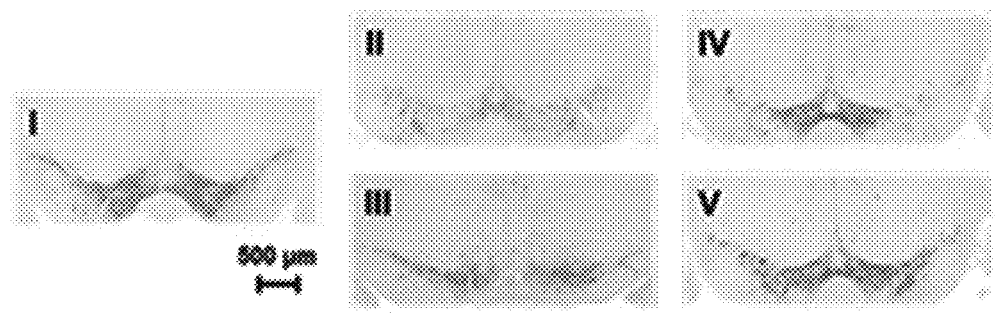
Figure 12G:
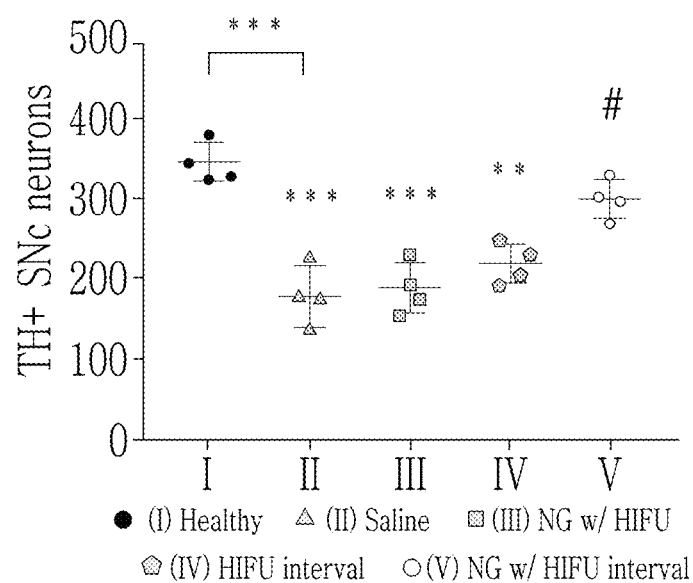

1-Methyl-4-phenyl-1,2,3,6-tetrahydropyridine (MPTP)-induced acute Parkinson's disease model mice were prepared, and their behavior was monitored according to the overall experiment timeline (see FIG. 12A). Since dopamine is important for the expression of learned fear, conditioning and expression of fear memory was investigated. The nanogenerator was intravenously injected to the mice in Group III and Group V at a volume of 80 mg/kg, and for accumulation of the nanogenerator, the brain tissues were immediately irradiated with ultrasound. With regard to the interval of ultrasound treatment in Group IV and Group V, the brain tissues were irradiated with ultrasound six times per day at an interval of 4 hours.

Group II (MPTP-treated mice) exhibited a noticeably decreased freezing level while fear was induced, as compared to Group I. No significant different was observed while the mice acquired fear memory; however, among the MPTP-treated groups, Group IV and Group V exhibited significantly high freezing levels while fear was induced (see FIG. 12). The insignificantly increased freezing level in Group IV implies that ultrasound itself can mechanically stimulate the nerve system in vivo. Furthermore, the nanogenerator accumulated in the brain tissue synergistically stimulated the nerve system of the mice in Group V in order to induce fear memory.

In addition, the change in the tyrosine hydrolase (TH) level during treatment of brain fragments based on immunohistochemistry (IHC) was investigated (see FIG. 12). TH is an enzyme that converts $_L$-tyrosine to $_L$-DOPA, which is a precursor of dopamine Therefore, a decreased number of TH reflects denaturation of dopaminergic neurons. The number of TH$^+$ neurons was noticeably decreased in the substantia nigra pars compacta (SNc) region in the MPTP-treated groups. In contrast, a larger number of TH$^+$ neurons were observed in Group D. This suggests that ultrasound DBS with nanogenerators suppresses denaturation of dopaminergic neurons in the nigrostriatal pathway.

The above-given description is intended only for illustrating the present invention, and any person having ordinary skill in the art to which the present invention is pertained, will be able to understand that the present invention can be realized in any form that has been modified to the extent that the fundamental characteristics of the present invention are maintained. Therefore, the disclosed Examples and Experimental Examples should be considered not from a restrictive viewpoint but from an illustrative viewpoint. The scope of the present invention is disclosed not in the above-described embodiments but in the following claims, and it should be understood that any alterations made to an extent equivalent to the claims are included in the present invention.

What is claimed is:

1. A method for increasing the blood-brain barrier permeability, the method comprising:
   (S1) a step of delivering a nanogenerator wherein the nanogenerator includes barium titanate (BaTiO$_3$) particles and a polydopamine layer covering the surface of the barium titanate particles carrying a nitric oxide (NO) donor wherein the nitric oxide donor is an ultrasound-responsive nitric oxide donor and is N,N'-di-sec-butyl-N,N'-dinitroso-1,4-phenylenediamine (BNN6, C$_{14}$H$_{22}$N$_4$O$_2$) to a site adjacent to the blood-brain barrier;
   (S2) a step of delivering a first triggering stimulus wherein the first triggering stimulus is ultrasound to an area where the nanogenerator has been delivered so as to release nitric oxide from the nanogenerator; and
   (S3) a step of allowing the released nitric oxide to activate matrix metallopeptidase-9 (MMP-9) and inducing the activated MMP-9 to weaken the tight junction between a cerebrovascular endothelial cell and another cerebrovascular endothelial cell.

2. The method for increasing the blood-brain barrier permeability according to claim 1, wherein the ultrasound is an ultrasound with a center frequency of 1.0 to 1.5 MHz and a duty cycle of 10% to 20%.

3. The method for increasing the blood brain barrier permeability according to claim 1, wherein in the step (S1), an active agent is delivered together with the nanogenerator to a site adjacent to the blood-brain barrier.

4. The method for increasing the blood-brain barrier permeability according to claim 3, wherein the active agent is a small molecule, a protein, a polysaccharide, a nucleic acid, a lipid, or a mixture of any two or more of these.

5. The method for increasing the blood-brain barrier permeability according to claim 3, wherein the active agent is a pharmaceutically active agent, a diagnostically active agent, or a combination of these.

6. The method for increasing the blood-brain barrier permeability according to claim 5, wherein the pharmaceutically active agent is a drug, a neurotrophic factor or a growth factor for treating any one or more diseases selected from the group consisting of a neurodegenerative disease, a neuropsychiatric disease, a brain tumor, a traumatic brain injury and a stroke.

7. The method for increasing the blood-brain barrier permeability according to claim 1, further comprising:
(S4) a step of allowing the nanogenerator to be delivered to the deep part of the brain by passing through between a cerebrovascular endothelial cell and a cerebrovascular endothelial cell, the step being performed after the step (S3); and
(S5) a step of delivering a second triggering stimulus to the nanogenerator that has been delivered to the deep part of the brain, so as to open the $Ca^{2+}$ influx channels of neurons present around the nanogenerator through a piezoelectric effect of the nanogenerator.

8. The method for increasing the blood-brain barrier permeability according to claim 7, wherein the second triggering stimulus is any one or more selected from the group consisting of ultrasound, sound, mechanical pressure, and resonance.

9. The method for increasing the blood-brain barrier permeability according to claim 7, wherein the method is used for alleviating the symptoms of a degenerative brain disease.

* * * * *